US008313750B2

(12) United States Patent
Chen et al.

(10) Patent No.: US 8,313,750 B2
(45) Date of Patent: Nov. 20, 2012

(54) ENTEROVIRUS TYPE 71 PROTEIN AND METHOD FOR PRODUCTION

(75) Inventors: Chuan-Mu Chen, Taichung (TW); Hsiao-Ling Chen, Taichung (TW)

(73) Assignee: National Chung Hsing University, Taichung (TW)

( * ) Notice: Subject to any disclaimer, the term of this patent is extended or adjusted under 35 U.S.C. 154(b) by 0 days.

(21) Appl. No.: 13/034,355

(22) Filed: Feb. 24, 2011

(65) Prior Publication Data

US 2011/0179508 A1 Jul. 21, 2011

Related U.S. Application Data

(62) Division of application No. 12/274,194, filed on Nov. 19, 2008, now Pat. No. 8,168,192.

(51) Int. Cl.
*A61K 39/12* (2006.01)
*C07H 21/02* (2006.01)
*C07H 21/04* (2006.01)

(52) U.S. Cl. ............... 424/199.1; 424/204.1; 424/205.1; 536/23.1; 536/23.72

(58) Field of Classification Search ........................ None
See application file for complete search history.

(56) References Cited

FOREIGN PATENT DOCUMENTS

WO WO 2007010291 A1 * 1/2007

OTHER PUBLICATIONS

Chen et al. Expression of VP1 protein in the milk of transgenic mice: A potential oral vaccine protects against enterovirus 71 infection. Vaccine 2008, vol. 26, p. 2882-2889.*

* cited by examiner

*Primary Examiner* — Louise Humphrey
(74) *Attorney, Agent, or Firm* — Occhiuti Rohlicek & Tsao LLP

(57) ABSTRACT

The invention provides a new type of a capsid protein VP1 of human enterovirus 71, named as MEL701-VP1 and functional/structural variants thereof, which is used for protection against enterovirus. The transgenic animal producing the protein, the composition comprising the protein and the method for production thereof are also provided.

2 Claims, 8 Drawing Sheets

```
                 1                                                     50
AF119796-TW1     GDRVADVIES  SIGDSVSRAL  TRALPAPTGQ  DTQVSSHRLD  TGKVPALQAA
AF176044-TW2     GDRVADVIES  SIGDSVSRAL  TRALPAPTGQ  DTQVSSHRLD  TGKVPALQAA
AF316321-Sin1    GDRVADVIES  SIGDSVSRAL  TQALPAPTGQ  NTQVSSHRLD  TGEVPALQAA
AF352027-Sin2    GDRVADVIES  SIGDSVSRAL  TQALPAPTGQ  NTQVSSHRLD  TGEVPALQAA
MEL701-EV71      GDRVADVIES  SIGDSVSRVL  TQALPAPTGQ  NTQVSSHRLD  TGEVPALQAA
Consensus        GDRVADVIES  SIGDSVSRAL  T-ALPAPTGQ  -TQVSSHRLD  TG-VPALQAA

                 51                                                    100
AF119796-TW1     EIGASSNASD  ESMIETRCVL  NSHSTAETTL  DSFFSRAGLV  GEIDLPLEGT
AF176044-TW2     EIGASSNASD  ESMIETRCVL  NSHSTAETTL  DSFFSRAGLV  GEIDLPLEGT
AF316321-Sin1    EIGASSNTSD  ESMIETRCVL  NSHSTAETTL  DSFFSRAGLV  GEIDLPLEGT
AF352027-Sin2    EIGASSNTSD  ESMIETRCVL  NSHSTAETTL  DSFFSRAGLV  GEIDLPLEGT
MEL701-EV71      ETGASSNTSD  ESMIETRCVL  NSHSTAETTL  DSFFSRAGLV  GEIDLPLEGT
Consensus        EIGASSN-SD  ESMIETRCVL  NSHSTAETTL  DSFFSRAGLV  GEIDLPLEGT

                 251                                               297
AF119796-TW1     IYMRMKHVRA  WIPRPMRNQN  YLFKANPNYA  GNSIKPTGAS  RTAITTL
AF176044-TW2     IYMRMKHVRA  WIPRPMRNQN  YLFKANPNYA  GNSIKPTGAS  RTAITTL
AF316321-Sin1    IYMRMKHVRA  WIPRPMRNQN  YLFKANPNYA  GNSIKPTGTS  RTAITTL
AF352027-Sin2    IYMRMKHVRA  WIPRPMRNQN  YLFKANPNYA  GNSIKPTGTS  RTAITTL
MEL701-EV71      IYMRMKHVRA  WIPRPMRNQN  YLFKANPNYA  GNSIKPTSTS  RTAITTL
Consensus        IYMRMKHVRA  WIPRPMRNQN  YLFKANPNYA  GNSIKPTG-S  RTAITTL
```

ENTEROVIRUS TYPE 71 PROTEIN AND METHOD FOR PRODUCTION

CROSS REFERENCE TO RELATED APPLICATIONS

This application is a division of U.S. patent application Ser. No. 12/274,194, filed Nov. 19, 2008, now issued as U.S. Pat. No. 8,168,192.

FIELD OF INVENTION

The invention is related to one new type of enterovirus protein and transgenic animals for producing and releasing the protein in milk.

BACKGROUND

Enterovirus 71 (EV71) is a member of the *Enterovirus* genus of the Picornaviridae family. EV 71 is the major cause of hand-foot-and-mouth disease (HFMD) in children. EV71 infection can be accompanied by a series of syndromes with or without central nervous system involvement including herpangina, aseptic meningitis, poliomyelitis-like paralysis and possibly fatal encephalitis. EV71 is a single-stranded RNA virus with a 7500-bp genome, enclosed by a capsid comprised of four coat proteins, VP1-VP4. The capsid protein VP1 of EV71 was reported to be the major antigenic coat protein and potent to act as an antiviral subunit vaccine, and VP4 to be an anchor-protein, linking VP1 to VP3 to form intact viral particles [Chow M et al., *Nature* 1987; 327: 482-486]. Since the viral particles (VPs) belonging to the Picornaviridae family can withstand human gastric acid and are infectious below pH 3.0, the VP1 would be expected as an antigen of an oral vaccine against entervirus.

Based on the genetic analysis of the EV71 epidemic in Taiwan, the sequences in the focal regions of 3C and 3'-non-coding region are different between the EV71 isolates from fatal cases and non-fatal cases [Shih SR et al., *Virus Res* 2000; 68: 127-136]. It was indicated that the VP1 protein of the EV71 was potential as an antigen in both the diagnosis and subunit vaccine development against EV71 [Yu CK et al., *J. Biomed. Sci.* 2000; 7:523-528]. Purified recombinant VP1 protein was defined as a neutralization determinant, with the ability to trigger vaccine-mediated immune responses in either Coxsackie virus B3-infected mice or swine [Henke A et al., *Antiviral Res* 2001; 49:49-54]. A VP1 subunit vaccine was produced in either bacteria or transgenic plants, which was effective against EV71 and foot-and-mouth disease virus [Wu CN et al., *Vaccine* 2002; 20:895-904]. However, it is still desired to develop a good vaccine effective for protection against EV71 and a feasible method for mass production of the vaccine antigen.

SUMMARY OF THE INVENTION

The invention features in a new type of the capsid protein VP1 from human enterovirus 71 (EV71) found in Taiwan, named as "MEL701-VP1."

Accordingly, in one respect, the invention provides a new type protein, which is a capsid protein VP1 of human enterovirus 71 (EV71), named as "MEL701-VP1," and functional/structural variant thereof. In one embodiment of the invention, the protein MEL701-VP1 has the amino acid sequence of SEQ ID NO: 1.

In another respect, the invention provides a nucleic acid molecule, encoding for the protein MEL701-VP1, and fragments thereof. In one embodiment of the invention, the protein MEL701-VP1 has the amino acid sequence of SEQ ID NO: 1.

In another yet respect, the invention provides a construct for expression the protein MEL701-VP1 in mammary gland cells of a non-human mammal comprises:

(a) a mammary gland specific promoter;

(b) a transgene having the nucleotide sequence coding for the protein MEL701 VP1; and (c) a polyadenylation signal sequence for stabilizing the expression of the transgene in mammary gland cells;

wherein (a), (b) and (c) are operatively linked in order from 5'-terminal to 3' terminal.

In one further respect, the invention provides a non-human transgenic mammal that produces in its mammary gland cells and secretes into its milk the protein EV71 VP1, particularly the protein MEL701-VP1 of the invention, wherein said transgenic mammal has stably integrated into its genome the exogenous gene construct.

The invention provides a method for production of a capsid protein VP1 of EV 71 (EV71 VP1) by the non-human transgenic mammal of the invention, wherein the protein is secreted by the mammary gland cells of the transgenic mammal and released into the milk. Through the method of the invention, a high-quantity and high-quality edible protein product will be obtained, which may be used as an antigen of an oral vaccine, or an active ingredient of a pharmaceutical composition or a food or feed product for protection against enterovirus, particularly EV 71.

In one further yet respect, the invention provides an edible product containing the protein MEL701-VP1, which has an effect for protection against enterovirus, particularly EV 71. In one embodiment of the invention, the product may be in the form of a pharmaceutical composition, drink, food or feed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a diagram showing the alignment of the protein MEL701-VP1 according to the invention, as compared with four of the well known capsid protein VP1s of EV71 strains.

DETAILED DESCRIPTION OF THE INVENTION

Figure 2A:
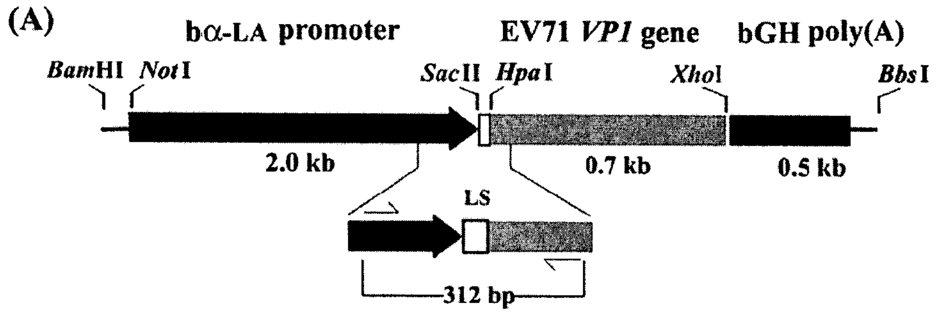
FIG. 2A is a diagram showing the construct of the αLA-VP1-bGH-poly(A) fusion gene that is one embodiment of the invention, which includes (a) a mammary gland specific promoter, (b) a transgene having the nucleotide sequence coding for the protein MEL701-VP1, and (c) a polyadenylation signal sequence.

The articles "a" and "an" as used herein refer to one or more than one (i.e., at least one) of the grammatical object of the article. By way of example, "an element" means one element or more than one element.

The invention provides a new type of the capsid protein VP1 of human enterovirus 71 (EV71), named as "MEL701-VP1", and variants thereof. In one embodiment of the invention, the protein MEL701-VP1 has the amino acid sequence of SEQ ID NO: 1. According to one embodiment of the invention, the protein "MEL701-VP1" was isolated from an autopsied throat swab specimen of a 2-year-old female child who was infected by EV71 and died in July, 2001.

In another embodiment of the invention, the protein MEL701-VP1 may be produced by the expression of a recombinant nucleic acid molecule, or chemically synthesized. In a preferred embodiment of the present invention, the protein may be produced into milk by a non-human transgenic mammal comprising an exogenous gene construct containing the transgene encoding the amino acid sequence of the protein MEL701-VP1, such as the protein of the amino acid sequence of SEQ ID NO: 1.

The term "EV71" as used herein refers to Enterovirus 71, a member of the *Enterovirus* genus of the Picornaviridae family. EV71 is a single-stranded RNA virus with a 7500-bp genome, enclosed by a capsid comprised of four coat proteins, VP1-VP4.

The term "VP1 or EV71 VP1" as used herein refers to the capsid protein VP1, one of the four coat proteins of EV71, which was reported to be the major antigenic coat protein and potent to act as an antiviral subunit vaccine.

The term "variant" or "variants" refers to a protein molecule having one or more mutations in the parent protein, such as a substitution, a deletion, an insertion and/or an addition to the parent protein. The "variant" or "variants" within this definition as used herein still have the EV71 VP1 activity in its activated, correctly folded form. The variant may be made by introducing one or more mutations in the protein having the amino acid sequence of the SEQ ID NO:1, e.g., at positions not essential to the antigenic activity. For instance, a substitution at a conservative amino acid residue with another one having similar chemical properties, is unlikely to affect the activity of said protein. Such mutations is also expected to preserve the antigenic activity of any structural variants of SEQ ID NO:1 thus made. In one embodiment, a structural/functional variant is at least 75% identical with the sequence of SEQ ID NO:1. In one embodiment, a structural/functional variant is 80% identical with the sequence of SEQ ID NO: 1. In another embodiment, a structural/functional variant is 90% identical with the sequence of SEQ ID NO:1. In one further embodiment, a structural/functional variant is 95% identical with the sequence of SEQ ID NO:1.

Modified protein from the sequence of SEQ ID NO: 1 also can be employed in this invention. Useful modifications within this context include, but are not limited to, those that alter post-translational modifications, size or active site, or that fuse this protein or portions thereof to another protein.

The invention also provides a nucleic acid molecule, encoding for the protein MEL701-VP1, and fragments thereof. In one embodiment of the invention, the protein MEL701-VP1 has the nucleotide sequence coding for the protein having the amino acid sequence of SEQ ID NO: 1, see Example 1 below. Anyone skilled in the art can prepare the nucleic acid molecule coding for the protein MEL701-VP1, particularly the amino acid sequence of SEQ ID NO: 1, according to the standard method or technologies.

Another object of the present invention is to provide a construct for expression of the protein MEL701-VP1 in mammary gland cells of a non-human mammal comprising:

(a) a mammary gland specific promoter;

(b) a transgene having the nucleotide sequence coding for the protein MEL701-VP1; and (c) a polyadenylation signal sequence for stabilizing the expression of the transgene in mammary gland cells;

wherein (a), (b) and (c) are operably linked in order from 5'-terminal to 3' terminal.

According to the invention, the transgene for expression of the protein MEL701-VP1 may be a sequence coding for the protein MEL701-VP1, such as the DNA coding for the amino acid sequence of SEQ ID NO: 1.

According to the invention, the promoter used may be any one that drives expression of VP1 in mammary gland cells. In one embodiment of the invention, the promoter is bovine alpha-lactalbumin (αLA) promoter. Furthermore, in one embodiment of the invention, a sequence that directs a secretion of the protein as expressed into milk may be inserted between the promoter and the transgene. Generally, any sequence known to direct the secretion of milk proteins in the art, such as a sequence encoding alphaS1-casein as being a 15-amino-acid signal peptide, may be used in the invention.

According to the invention, any polyadenylation signal sequence for stabilizing the expression of the transgene in mammary gland cells may be used. In one embodiment of the invention, the sequence for stabilization is bovine GH polyadenylation signal sequence (bGH poly(A)).

In one example of the invention, alphaLA-CN-VP transgene was constructed for used in microinjection to a mammal to produce a transgenic mammal (see Example 2).

The present invention further provides a non-human transgenic mammal that produces in its mammary gland cells and secretes into its milk at detectable levels the protein EV71 VP1 having the antigenic activity, wherein said transgenic mammal has stably integrated into its genome an exogenous gene construct above. In one embodiment of the invention, the protein is the protein MEL701-VP1, particularly the protein having the amino acid sequence of SEQ ID NO: 1.

The term "animal" used herein refers to any mammalian animal except a human. It also includes an individual animal in all stages of development, including embryonic and fetal stages. A "transgenic" animal is any animal containing cells that bear genetic information received, directly or indirectly, by deliberate genetic manipulation at the subcellular level, such as by the infection or genetic_microinjection with recombinant virus. The transgenic animals of the invention are other than human, and produce milk. Farm animals (pigs, goats, sheep, cows, horses, rabbits and the like), rodents (such as rats and mice), and domestic pets (for example, cats and dogs) are included in the scope of this invention. In one embodiment of the invention, the transgenic mammal as used may be any one selected from the group consisting of mouse, rat, pig, goat, sheep, cow, horse, rabbit, cat and dog. In a preferred embodiment of the invention, the transgenic mammal as used is any one selected from the group consisting of mouse, rat, pig, goat, sheep, cow, horse and rabbit. As stated in Example 3 below, homozygous and heterozygous transgenic mice were successfully prepared. Furthermore, the transgenic mammal according to the invention can secret and release the recombinant protein into the milk. As evidenced in Example 6, the milk secreted by the transgenic mice according to the invention had antiviral protective effect against EV71.

The invention provides a method for production of the protein EV71 VP1 by the non-human transgenic mammal of the invention, wherein the protein is secreted by the mammary gland cells of the transgenic mammal and released into the milk.

The invention also provides an edible product containing the protein MEL701-VP1, which has an effect for protection against enterovirus, particularly EV 71, which may be in the form of a pharmaceutical composition, drink, food or feed. As the protein MEL701-VP1 has the antigenic activity against enterovirus, and is highly withstanding human gastric acid, the protein MEL701-VP1 can be used as an active ingredient in a composition for oral administration providing an efficacy in protection against enterovirus, particularly EV 71. An example of such a composition may be an edible product, such as a pharmaceutical composition, a drink, food or feed. In one embodiment of the invention, the protein MEL701-VP1 may be prepared as an oral vaccine. The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol and combinations thereof.

The pharmaceutical composition of the present invention may be constituted into any form suitable for the mode of administration selected. For example, compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In addition to standard carriers, an oral pharmaceutical composition of the present invention may be supplemented with one or more excipients that are normally employed in oral formulations, such as surfactants, solubilizers, stabilizers, emulsifiers, thickeners, coloring agents, sweetening agents, flavoring agents, and preservatives. Such excipients are well known to those skilled in the art.

The protein MEL701-VP1 may also be prepared in the form of drink, food or feed. Examples of them include but not limited to dairy products, fermented dairy products, soft drinks, sport drinks, healthcare food, elder food, candies, and gum, containing the protein MEL701-VP1. If desired, the products may then be blended with additional spices or other additives.

Furthermore, since the protein MEL701-VP1 according to the invention is one new type of VP1 protein, which is the major antigenic coat protein of EV71, it is potential for used in preparation of an oral vaccine for protection of a child from the infection of EV71, which were well supported by Examples 6 and 7 below.

The present invention will now be described more specifically with reference to the following embodiments, which are provided for the purpose of demonstration rather than limitation.

EXAMPLE 1

Virus and Cell Culture

A newly-identified fatal strain of EV71 was isolated from an autopsied throat swab specimen of a 2-year-old female child who was infected by EV71 and died in July, 2001, named as the isolate "MEL701-EV71." The virus culture fluid was purified with high concentration antibiotics (500 U/ml Penicillin, 500 μg/ml Streptomycin sulfate, 10 μg/ml Amphotericin B). African green monkey kidney cells (Vero cells, ATCC CCL-81) were used for the propagation of virus. These cells were cultivated in Dulbecco's Modified Eagle Medium (DMEM) and 5% fetal bovine serum (FBS) at 37° C. When cytopathic effect (CPE) was observed in 80% of the Vero cells, culture fluid was purified with precipitation and centrifugation after two freeze-thaw cycles, as described previously [Chen HL et al., *Vaccine* 2008; 26: 891-898]. The virus stock was stored at −80° C.

EXAMPLE 2

Gene Construction and Alignment of EV71 Sequences

The virus RNA was extracted from 200 μl of the virus stock of the isolated strain "MEL701-EV1" by using 1 ml Tri-Reagent (MRC Inc., USA). Reverse-transcriptase (RT)-PCR was performed using the viral RNA in order to obtain a full length cDNA. With the degenerate primer sets, VP1(+): 5'-AGTTAACGGGG GACAGAGTGGCA-3' (SEQ ID NO:2) and VP1(−): 5'-TGCTCGAGCTTTCAAAGGGTAG-TAA-3' (SEQ ID NO:3), the VP1 sequence was amplified and inserted into a mouse mammary gland-specific expression vector named "pCR-αLA-CN", which contains a bovine alpha-lactalbumin (αLA) promoter operably linked to a alphaS1-casein leader sequence and a bovine GH polyadenylation signal sequence, to obtain an expression vector named as "pCR-αLA-CN-VP1." Transformation of *E. Coli* DH5α and the plasmid DNA extraction were performed prior to DNA sequencing with the BigDye Terminator kit (Perkin Elmer Applied Biosystems, Foster, Calif.).

The nucleotide and peptide sequences of the capsid proteins VP1 were obtained from the new isolated strain MEL701-EV71, which were submitted to GenBank with accession numbers of EU099991, named as "MEL701-VP1." These sequences were aligned with four well-known EV71 isolates for homology determination, two isolated from Taiwan (AF119796 and AF176044) and two from Singapore (AF31632 and AF352027), see FIG. 1.

These data indicated a relatively closer relationship between the newly identified EV71 strain and the two Singapore strains, and they also showed several potential mutation hot-spots in the EV71 capsid protein sequence, which are very likely to contribute to the diversity of EV71's virulence (data shown in the Table 1).

TABLE 1

Homology of VP1-VP4 amino acid sequences of different EV71 isolates

| EV71 Isolates | Percentage Homology to amino acid Sequence of: MEL-EV71* | Taiwan-1 AF119796 | Taiwain-2 AF176044 | Singapore-1 AF316321 | Singapore-2 AF352027 |
|---|---|---|---|---|---|
| MEL-EV71 | 100 | | | | |
| Taiwan-1 AF119796 | 96.44 | 100 | | | |
| Taiwain-2 AF176044 | 96.44 | 99.65 | 100 | | |
| Singapore-1 AF316321 | 98.96 | 97.33 | 97.33 | 100 | |
| Singapore-2 AF352027 | 98.96 | 97.33 | 97.33 | 100 | 100 |

*New identified EV71 clone (MEL701 isolate) in this study. GenBank accession numbers: EU099991-4.

EXAMPLE 3

Production and Identification for Transgene

Figure 2B:
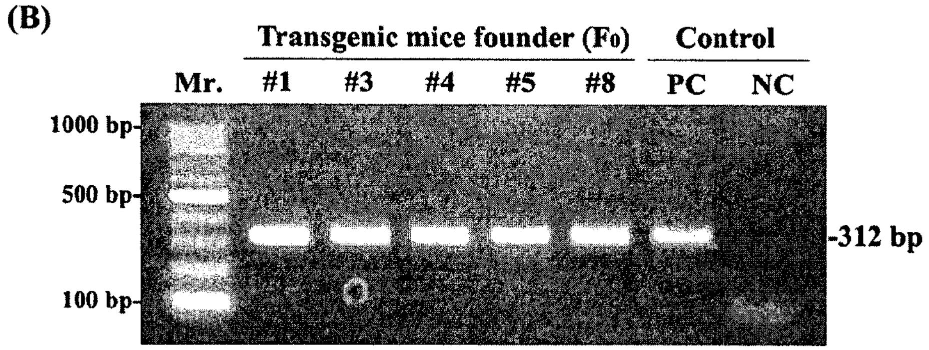
FIG. 2B is an image showing the result of the rapid screening by PCR amplification of the transgenic mice founders (Mouse Nos. #1, #3, #4, #5, and #8) and the positive and negative controls (marked by PC and NC, respectively). In the transgenic mouse founders in each of which the 312-bp sequence has been found to confirm that the transgene microinjection was successfully done.
Figure 2C:
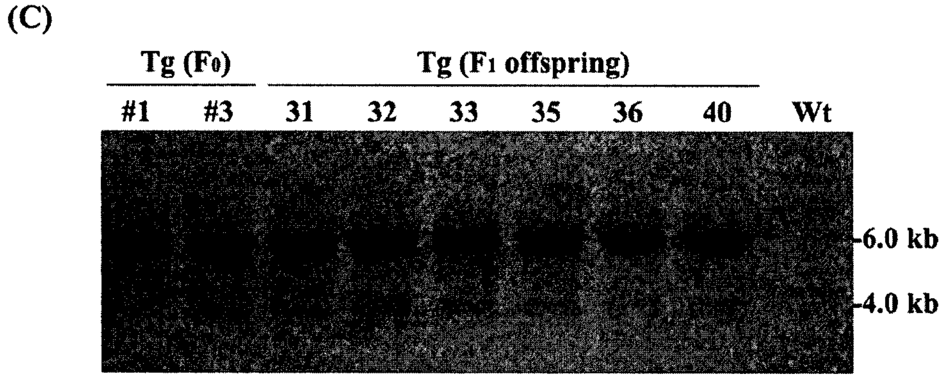
FIG. 2C is an image showing the Southern blots showing the integration patterns of αLA-CN-MEL701-VP1 in the transgenic mice (Mouse Nos. #1 and #3) and their F1 offsprings (marked by the Offspring Nos. 31, 32, 33, 35, 36 and 40).

A 3.2-kb αLA-CN-VP1 transgene (FIG. 2A) was directly microinjected into pronuclear-stage mouse embryos and transferred into the fallopian tubes of recipient females. After parturition, 32 newborn mice were obtained and underwent PCR screening, and five newborn mice, named Tg-VP1-$F_0$-#1, -#3, -#0.4, -#5 and -#8, were identified to be successfully integrated with the αLA-CN-VP1 transgene (FIG. 2B). Breeding lines were established from all of the five transgenic founder mice by crossing with normal ICR mice. The integration pattern of the foreign gene was demonstrated by Southern blot analysis (FIG. 2C). Two transgenic founders (Tg-VP1-$F_0$-#1 and -#3) were found to possess different transgenic patterns. The multiple integrated copies of the transgene were found to be stably germ-line transmitted among 4 (2 females and 2 males) out of 5 transgenic founders.

EXAMPLE 4

Production and Determination for Transgenic Mouse

The αLA-CN-VP1 transgenic CD-1 (ICR) mice were generated by pronuclear microinjection of a 3.2-kb transgene fragment comprising the bovine αLA promoter, αS1-casein signal peptide leader sequence, the cDNA coding for MEL701-VP1 and bovine GH polyadenylation signal sequence, which was obtained from the pCR-αLA-CN-VP1 plasmid with BamH I-Bbs I double-digestion and was purified by two rounds of $CsCl_2$ gradient ultra-centrifugation, as described previously [Wu SC et al., *J Agric Food Chem* 2007; 55: 4670-4677]. The resulting pups were rapidly screened for the foreign gene by PCR analysis of tail genomic DNA with the primer set αLA124(+): 5'-CTCTCTTGTCATCCTCT-TCC-3' (SEQ ID NO:4) and VP1(−): 5'-TTACC TGCGT GTTCT GACCT-3' (SEQ ID NO:5). The results were confirmed by the Southern blot analysis as described in Wu's reference [Wu SC et al., ut supra].

Figure 3A:
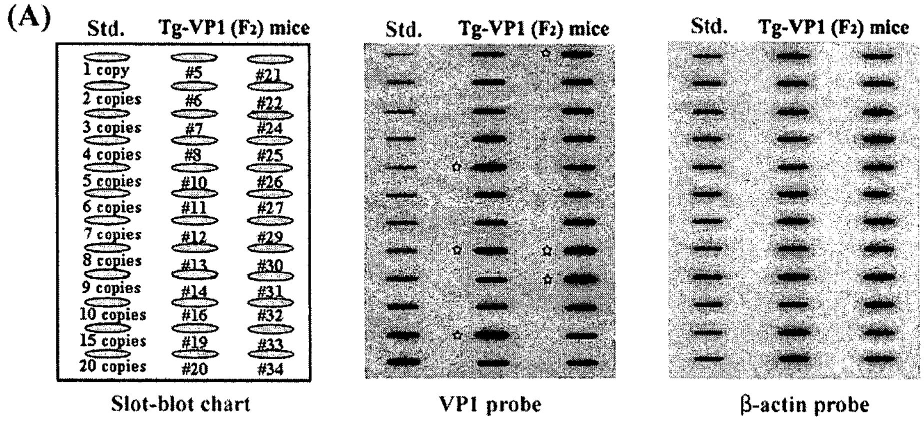
FIG. 3A is a diagram showing the VP1 transgenic copies in the genomes of the transgenic offspring, wherein the slot-blot chart in the left panel indicates the location of each arrayed DNA sample of the transgene copy standards and the offsprings marked by the Offspring Nos.; in the middle panel, ten micrograms of the genomic DNA were blotted onto the nitrocellulose membrane and hybridized with a 0.7-kb VP1 probe; and in the right panel, the filter was stripped and rehybridized with a 0.8 kb probe from the mouse β-actin gene that was used as an internal control. Copy standards were prepared by mixing 10 μg of the non-transgenic mouse' tail DNA with a known amount of the transgene plasmid DNA to produce transgene copy standards as shown in the lane Std.
Figure 3B:
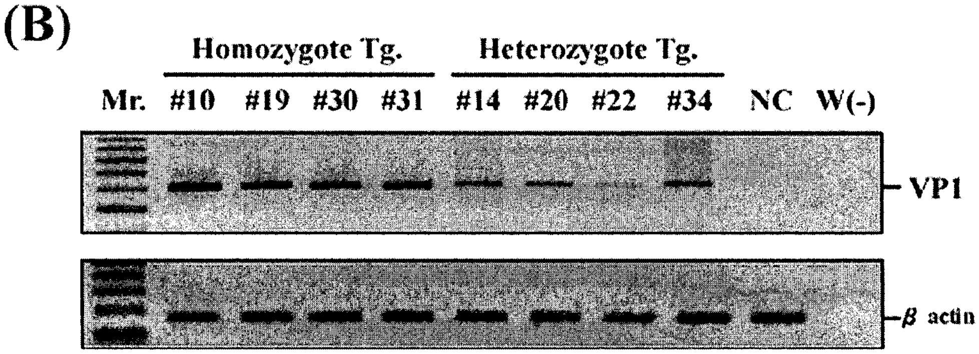
FIG. 3B is an image showing the level of the VP1 mRNA expression in the homozygous and heterozygous transgenic mice detected by reverse-transcriptional polymerase chain reaction (RT-PCR). NC represents normal mouse mammary gland mRNA as a template for the negative control. Results were shown by the representatives of the three experiments.
Figure 3C:
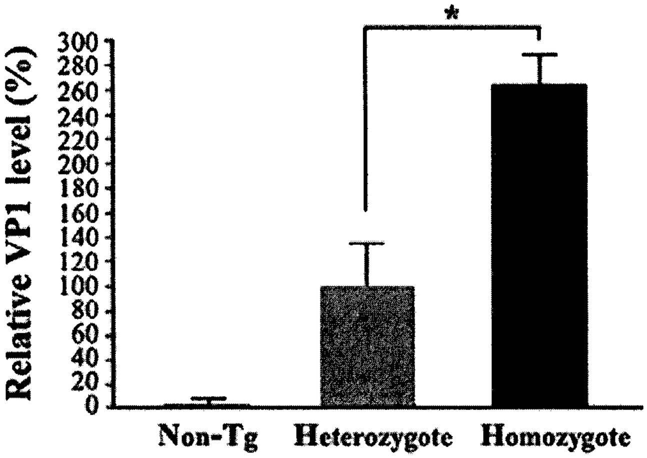
FIG. 3C is an image showing the relative VP1 mRNA expression levels in homozygous and heterozygous transgenic mice quantified by a densitometer. The signal of the β-actin RT-PCR product in each sample was used as an internal control in the VP1 signal calculation.

For identification of heterozygous ($VP1^{+/-}$) and homozygous ($VP1^{+/+}$) genotypes in the $F_2$ generation of transgenic breeding lines, first detected the genotypes of αLA-CN-VP 1 transgenic mice were detected by slot blots and offspring test-crosses. The recombinant MEL701-EV71 mRNA expression levels in the mammary glands of heterozygous and homozygous transgenic mice were detected by reverse transcription-polymerase chain reaction (RT-PCR), as described previously [Wu SC et al., ut supra]. The results indicated that six transgenic mice (Tg-VP1-F2-#10, -#13, -#19, -#21, -#30 and -#31) contained more copies of the transgene than others when the comparative nucleic acid probe was normalized to the mouse β-actin hybridization signal (FIG. 3A, right panel). After the offspring test-cross, it was ascertained that these six transgenic mice carried a homozygous transgene whereas the others were heterozygous. To characterize the expression level of transgenic VP1 mRNA, semi-quantitative RT-PCR was performed. As shown in FIG. 3B, a 320 bp RT-PCR product from the VP1 transcript was amplified from the mammary gland of heterozygous and homozygous lactating transgenic mice with different intensities. To quantify the level of VP1 mRNA in the transgenic heterozygous and homozygous lines, densitometric analysis was performed (FIG. 3C). The relative VP1 mRNA expression level was significantly increased by 1.6-fold in examined homozygous mice relative to that of heterozygous transgenic mice ($P<0.05$).

EXAMPLE 5

Detection of Protein Expression in Mammary Glands and Milk

Freshly dissected mammary-gland tissue from transgenic and non-transgenic mice at the D14 lactating stage was fixed in paraformaldehyde and embedded with O.C.T. compound (Tissue-Tek®, Sakura, Japan). After micro-dissection of the frozen tissue, 5 μm tissue sections were incubated with mouse anti-EV71 monoclonal antibody (Light Diagnosis 3324, Chemicon International, Inc., Temecula, Calif.) and FITC-labeled secondary antibody. The slides were observed under a microscope equipped with epifluorescence optics.

For immunoblot analysis, milk was collected from the lactating female transgenic mice and proteins were analyzed by SDS-PAGE and Western blotting. The blots were hybridized with a rabbit anti-EV71 polyclonal antibody and HRP-conjugated anti-rabbit IgG antibody. The blot was then developed with the chemiluminescent ECL™ detection system (Amersham Biosciences, UK). A quantitative ELISA was performed using the same antibodies as described above. The protein EV 71 VP1 was detected using o-phenylenediamine (OPD; Sigma, St. Louis, Mo.) dissolved in citrate buffer (pH 5.0) in the presence of 0.01% $H_2O_2$. The results were read using an ELISA microplate reader (Bio-Rad Lab., USA) at 490 nm.

To verify recombinant VP1 protein expression and secretion in the milk of transgenic mice, fluorescence in situ hybridization (FISH) immuno-staining of mammary gland tissue sections was performed. Localized and relatively high accumulation of VP1 protein within the mammary acini and lumen of lactiferous tubules was visualized by an epifluorescence microscope in homozygous transgenic mice ($VP1^{+/+}$) at the D14 lactating stage. There was no detectable FITC signal on sections of wild type CD-1 (ICR) mouse ($VP1^{31\ /-}$) mammary gland.

Figure 4A:
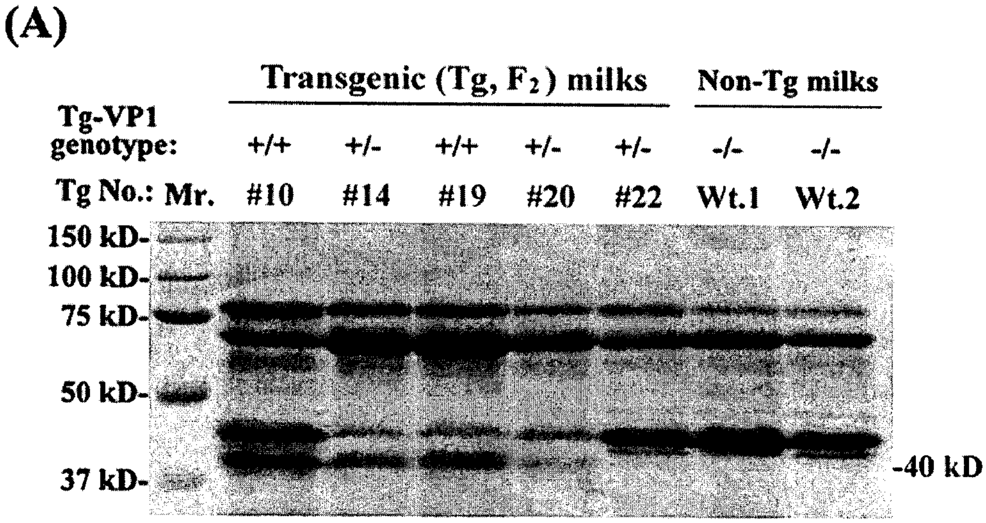
FIG. 4A is an image of a SDS-PAGE showing the expression of the protein MEL701-VP1 in the milk of homozygous and heterozygous transgenic mice.
Figure 4B:
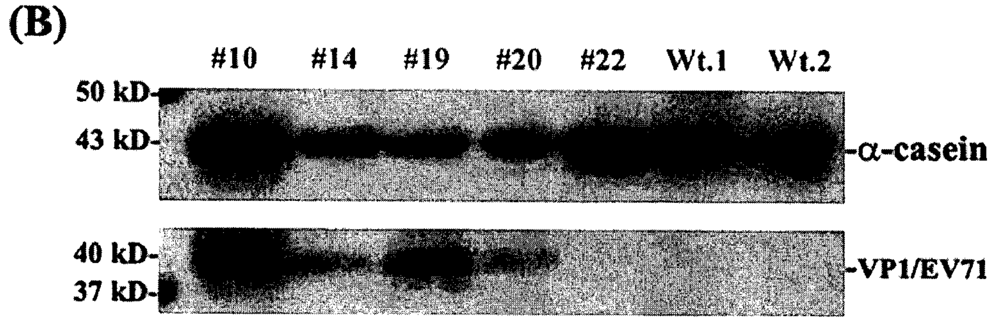
FIG. 4B is an image of a western blotting showing the expression of the protein MEL701-VP1 in the milk of homozygous and heterozygous transgenic mice.

The milk from two homozygous transgenic lines (Tg-VP1-F2-#10 and -#19) exhibited higher VP1 protein expression than that of two heterozygous transgenic lines (Tg-VP1-F2-#14 and -#20) (FIG. 4A), while no polypeptides characteristic of the VP1 protein were detected in the milk from the control group and the heterozygous transgenic line (Tg-VP1-F2-#22) (FIG. 4B). The concentration of the recombinant protein MEL701-VP1 in the milk produced from homozygous transgenic lines (2.51±0.63 mg/ml) was significantly higher than that of heterozygous mice (1.08±0.41 mg/ml) when quantified by the ELISA assay ($P<0.05$).

EXAMPLE 6

Establishment of Animal Model for EV71 Challenge

To establish an appropriate animal model to demonstrate the antiviral activity of the MEL701-VP1 containing milk, the mouse littermates suckling either the milk of the transgenic or non-transgenic animals were intra-peritoneally injected with 100 μl ($3.2\times10^5$ $TCID_{50}$/ml) purified EV71 fluid, according to Yu et al. [Wang J H et al., *Vaccine* 2003; 21:3721-3729], or 100 μl phosphate-buffered saline (PBS) solution as a control group. Firstly, in order to determine the optimal timing, an age-dependent challenge assay was performed. Seven-day, six-day and four-day-old postnatal normal mice were challenged with virus fluids (EV71 group) and their body weights were recorded each day thereafter and compared to those of the control (PBS group). Normal CD-1 (ICR) mice that were orally administered VP1 transgenic milk were challenged at 4 days of age, which was previously shown to be the best timing, and body weights as well as health conditions were recorded each day until 21 days post-EV71 infection. Animals were housed and handled according to guidelines of the Animal Care Committee of the National Chung Hsing University.

Figure 5:
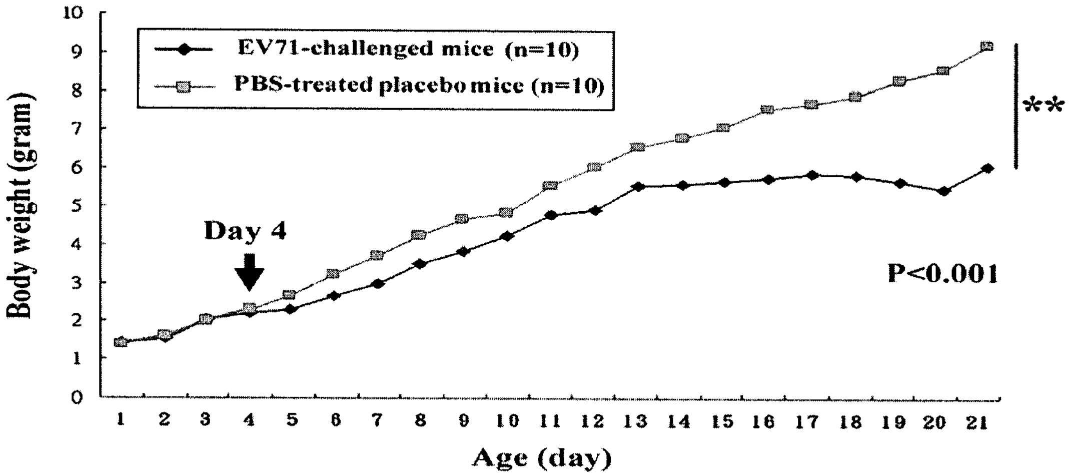
FIG. 5 is a diagram showing the changes of body weights of the 4-day-old mice neonatal pups of normal mouse littermates (n=10), as marked by "-♦-EV71-challenged mice" after challenged by EV71, as compared with the negative control, treated with PBS (n=10), as marked by "-■-PBS-treated placebo mice." ** indicates $p<0.001$.

An age-dependent EV71 challenge assay was performed for the establishment of an animal model. Normal mouse pups at 7-day, 6-day and 4-day postnatal ages were challenged with 100 μl of EV71 fluid containing $3.2\times10^5$ $TCID_{50}$ $ml^{-1}$, as test groups (EV71), or 100 μl of phosphate-buffered saline solution, as control groups (PBS). In the 7-day-old and 6-day-old challenged mouse pups (n=10), no significant body weight loss was detected through the 21-day observation period ($P>0.05$). In the 4-day-old challenge groups (FIG. 5), the average body weights were significantly decreased in the EV71-infected pups (n=9) compared with the PBS-treated control pups (n=8) during the three weeks of measurements ($P<0.001$). Furthermore, a series of EV71-infected pathological symptoms, such as skin lesions and limb paralysis, were observed in pups after EV71 challenge for three days. Therefore, 4 days after birth was chosen as the EV71 inoculation point in the animal model.

EXAMPLE 7

Determination for Antiviral Protective Effect of MEL701 VP1

Figure 6:
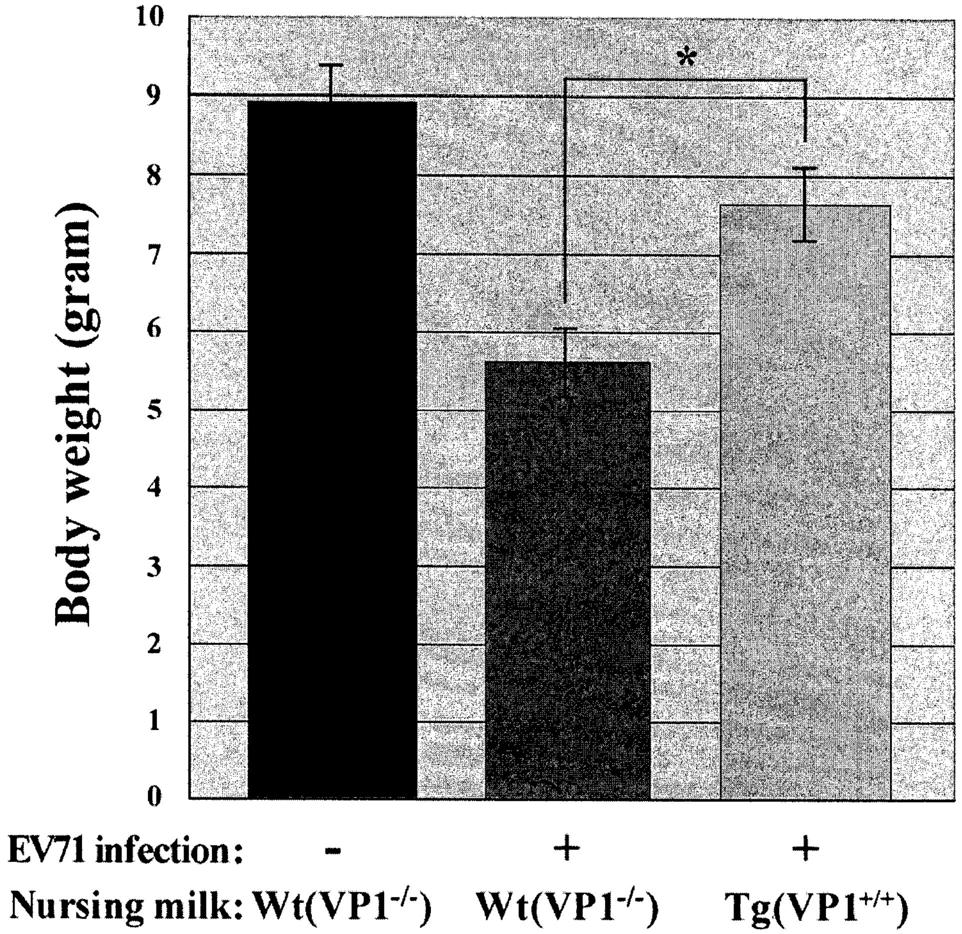
FIG. 6 is a diagram showing the changes of body weights of the mice orally administered with the transgenic animals' milk (Tg group, n=8) or normal milk as controls (Wt groups, n=10), were challenged at the postnatal age of 4 days with or without EV71. * indicates $p<0.05$.

To demonstrate the antiviral effect of VP1-containing milk as a potential oral vaccine, normal mouse littermates suckling VP1-enriched milk produced from homozygous ($VP1^{+/+}$) transgenic females (Tg, n=8) or non-transgenic ($VP1^{-/-}$) milk (Wt, n=10) were intra-peritoneally injected with 100 μl of purified EV71 fluid ($3.2\times10^5$ $TCID_{50}$ $ml^{-1}$) at 4 days of age. As shown in FIG. 6, body weight gains during the 3-week experimental period were recorded and data showed that the pup growth curve was significantly improved in the experimental group who were fed VP1-containing milk, when compared with mice from the control group who were fed non-transgenic milk ($P<0.05$). A series of EV71 related pathological symptoms including skin lesions (80%; 8/10) and limb paralysis (70%; 7/10) presented in the virus challenged control group, while the symptoms were absence in the VP1-administered experimental group. These data clearly demonstrated that neonatal mice orally administered VP1 protein possessed immunological protection against EV71 infection.

The ELISA plates were coated overnight with 2 μg/ml of bacterial purified VP1 dissolved in carbonate coating buffer (15 mM $Na_2CO_3$, 35 mM $NaHCO_3$, pH 9.6). Following incubation with 1% bovine serum albumin (BSA) in PBS for 2 h at room temperature to prevent non-specific binding, serial dilutions of test sera were added to each well and incubated overnight at 4° C. After washing with PBST (PBS and 0.5% Tween-20), bound proteins were detected using HPRT-conjugated anti-mouse IgG (1:10000; Mouse IgG ELISA Quantitation Kit; Bethyl Laboratories, Inc.). As a substrate, 100 μl TMB (3,3',5,5'-tetramethylbenzidine) was used, and the reaction was stopped by 100 μl 1N $H_2SO_4$. Absorbance was measured at 450 nm. The concentration for IgG is indicated as E.U., and one E.U. of IgG is 1.8 ng/ml serum.

Figure 7:
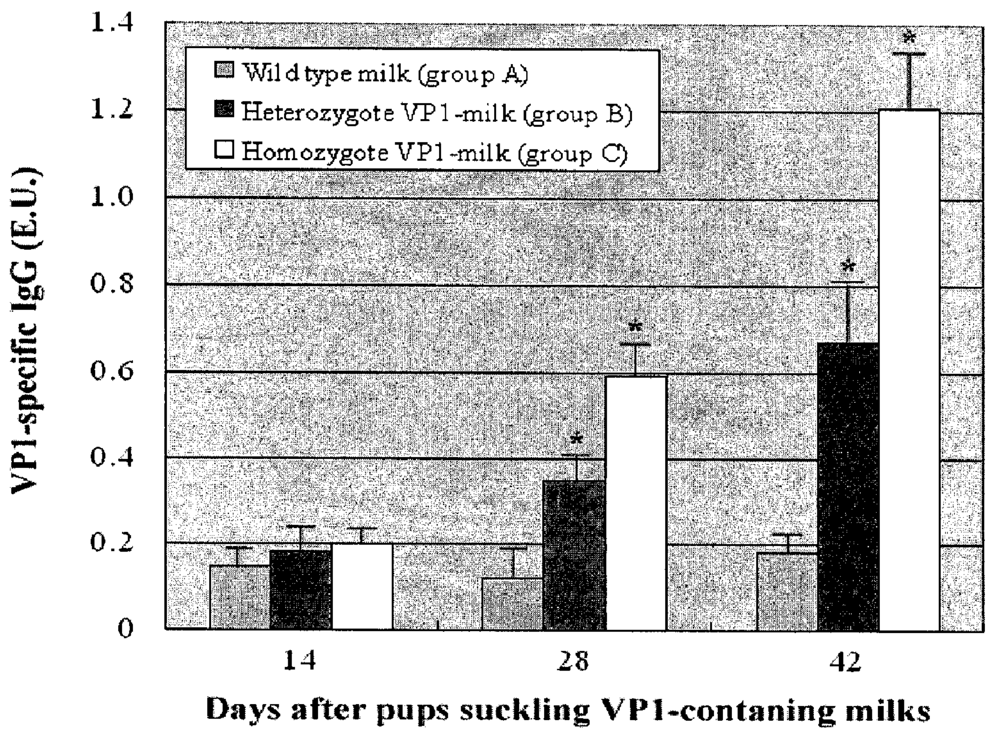
FIG. 7 is a diagram showing the results of the ELISA detection on the levels of the IgG antibodies against EV71 in the sera of the mice orally vaccinated with MEL701-VP1-enriched milk derived from the transgenic mice (heterozygous transgenic mice, Group B and homozygous transgenic mice, Group C) and the milk of the control group (Wild type mice, Group A). The results were presented as mean±SEM. * indicates $p<0.05$.

The specific anti-VP1 IgG antibody can be detected in the serum of experimental mice at days 28 and 42 post VP1-containing milks administration (FIG. 7). As shown in FIG. 7, from day to day, the amount of VP1 increased, and homozygote VP1 milk had the most significantly upgrade.

EXAMPLE 8

Antiviral Effect in Serum Neutralization Assay

The Blood sera were collected from mice that were orally administered either transgenic milk (Tg) or wild-type milk (WT) at the age of 6-8 weeks. Sera were serially diluted from 1:5, 1:10 to 1:50, and combined with 200 μl containing 100 tissue culture infectivity doses (TCID) EV71 for 1 hour at 37° C. The final solution was added to 96-well cell culture plates and co-cultured with Vero cells ($2.5\times10^4$ cells/well) for 5 days. According to cytopathic effect (CPE), living cell numbers were quantified by enumerating the cells able to exclude trypan blue. These numbers were recorded to determine the antiviral effect of mouse sera. Cell survival rates were calculated; a density of $6.0\times10^4$ cells/well was recorded for the standard control.

Figure 8:
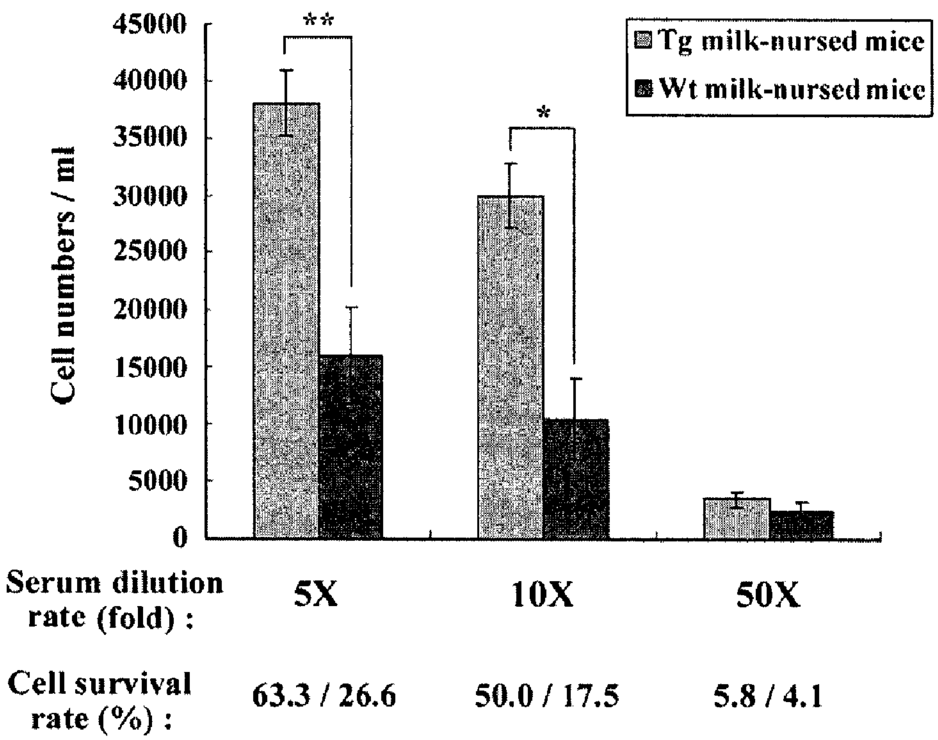
FIG. 8 is a diagram showing the results of serum neutralization assay for antiviral protective effect against EV 71 of the mice orally vaccinated with MEL 701 VP1-enriched milk derived from transgenic mice (Tg milk-nursed mice) and the milk from the control group (Wt milk-nursed mice) in terms of the cell survivals. The results were presented as mean±SEM. * indicates $p<0.05$, ** indicates $p<0.01$.

Sera from mice suckling VP1-enriched transgenic milk or non-transgenic milk were obtained at 6-8 weeks of age to determine their ability to inhibit EV71 infection in vitro. Serially-diluted serum at 5×, 10×, and 50× was co-incubated with EV71 and then added to Vero cell culture medium. During the five-day observation period, the EV71-infected cells showed obvious cytopathic effect (CPE), which allowed us to distinguish them from normal Vero cells and record the living cell numbers. The results demonstrated that significant antiviral effects were achieved by viral neutralization in the 5× diluted ($P<0.001$) and 10× diluted ($P<0.05$) immunized blood serum of mice fed with VP1-enriched transgenic milk when compared with that from the normal milk-nursed control mice (FIG. 8).

Statistical Analysis

Experimental values are expressed as the mean±standard deviation (SD). All data were analyzed in the randomized complete block design using the General Linear Model procedures of SAS (SAS Institute Inc., Cary, N.C.). A difference between two means was presented as $P<0.05$ (*) and $P<0.01$ (**).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An isolated nucleotide sequence encoding a MEL701-VP1 protein, wherein the MEL701-VP1 protein is a capsid protein of human enterovirus 71 (EV71) having the amino acid sequence of SEQ ID NO: 1.

2. A recombinant DNA construct comprising the isolated nucleotide sequence of claim 1.

* * * * *

SEQUENCE LISTING

```
<160> NUMBER OF SEQ ID NOS: 5

<210> SEQ ID NO 1
<211> LENGTH: 297
<212> TYPE: PRT
<213> ORGANISM: enterovirus 71

<400> SEQUENCE: 1

Gly Asp Arg Val Ala Asp Val Ile Glu Ser Ser Ile Gly Asp Ser Val
                5                   10                  15

Ser Arg Val Leu Thr Gln Ala Leu Pro Ala Pro Thr Gly Gln Asn Thr
            20                  25                  30

Gln Val Ser Ser His Arg Leu Asp Thr Gly Glu Val Pro Ala Leu Gln
        35                  40                  45

Ala Ala Glu Thr Gly Ala Ser Ser Asn Thr Ser Asp Glu Ser Met Ile
    50                  55                  60

Glu Thr Arg Cys Val Leu Asn Ser His Ser Thr Ala Glu Thr Thr Leu
65                  70                  75                  80

Asp Ser Phe Phe Ser Arg Ala Gly Leu Val Gly Glu Ile Asp Leu Pro
                85                  90                  95

Leu Glu Gly Thr Thr Asn Pro Asn Gly Tyr Ala Asn Trp Asp Ile Asp
            100                 105                 110

Ile Thr Gly Tyr Ala Gln Met Arg Arg Lys Val Glu Leu Phe Thr Tyr
        115                 120                 125

Met Arg Phe Asp Ala Glu Phe Thr Phe Val Ala Cys Thr Pro Thr Gly
    130                 135                 140

Glu Val Val Pro Gln Leu Leu Gln Tyr Met Phe Val Pro Pro Gly Ala
145                 150                 155                 160

Pro Lys Pro Glu Ser Arg Glu Ser Leu Ala Trp Gln Thr Ala Thr Asn
                165                 170                 175

Pro Ser Val Phe Val Lys Leu Thr Asp Pro Pro Ala Gln Val Ser Val
            180                 185                 190
```

-continued

```
Pro Phe Met Ser Pro Ala Ser Ala Tyr Gln Trp Phe Tyr Asp Gly Tyr
        195                 200                 205

Pro Thr Phe Gly Glu His Lys Gln Glu Lys Asp Leu Glu Tyr Gly Ala
    210                 215                 220

Cys Pro Asn Asn Met Met Gly Thr Phe Ser Val Arg Thr Val Gly Ser
225                 230                 235                 240

Ser Lys Ser Lys Tyr Pro Leu Val Val Arg Ile Tyr Met Arg Met Lys
                245                 250                 255

His Val Arg Ala Trp Ile Pro Arg Pro Met Arg Asn Gln Asn Tyr Leu
            260                 265                 270

Phe Lys Ala Asn Pro Asn Tyr Ala Gly Asn Ser Ile Lys Pro Thr Ser
        275                 280                 285

Thr Ser Arg Thr Ala Ile Thr Thr Leu
    290                 295


<210> SEQ ID NO 2
<211> LENGTH: 23
<212> TYPE: DNA
<213> ORGANISM: Artificial
<220> FEATURE:
<223> OTHER INFORMATION: Primer

<400> SEQUENCE: 2

agttaacggg ggacagagtg gca                                            23


<210> SEQ ID NO 3
<211> LENGTH: 25
<212> TYPE: DNA
<213> ORGANISM: Artificial
<220> FEATURE:
<223> OTHER INFORMATION: Primer

<400> SEQUENCE: 3

tgctcgagct ttcaaagggt agtaa                                          25


<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4

ctctcttgtc atcctcttcc                                                20


<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5

ttacctgcgt gttctgacct                                                20
```